United States Patent
Giles et al.

(10) Patent No.: US 6,592,856 B2
(45) Date of Patent: *Jul. 15, 2003

(54) SHAMPOO COMPOSITIONS

(75) Inventors: Colin Christopher David Giles, Wirral (GB); Frances Ann Ellis, Wirral (GB); Andrew Malcolm Murray, Wirral (GB); Matthew Leslie Pearce, Wirral (GB); Pamela Eileen Red, Wirral (GB)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/022,703

(22) Filed: Dec. 13, 2001

(65) Prior Publication Data

US 2002/0071819 A1 Jun. 13, 2002

Related U.S. Application Data

(62) Division of application No. 09/496,574, filed on Feb. 2, 2000, now Pat. No. 6,350,441.

(30) Foreign Application Priority Data

Feb. 5, 1999 (GB) .............................................. 9902629

(51) Int. Cl.$^7$ ............................. A61K 7/06; A61K 7/075
(52) U.S. Cl. ................ 424/70.12; 424/70.1; 424/70.11; 424/70.13; 424/70.21; 424/70.22; 510/119; 510/122
(58) Field of Search ............................. 424/70.1, 70.11, 424/70.12, 70.13, 70.21, 70.22, 401; 510/119, 122

(56) References Cited

FOREIGN PATENT DOCUMENTS

| | | |
|---|---|---|
| EP | 0432951 | 6/1991 |
| EP | 0529883 | 3/1993 |
| WO | 96/25144 | 8/1996 |
| WO | 97/35547 | 10/1997 |
| WO | 98/04240 | * 2/1998 |
| WO | 98/16538 | 4/1998 |
| WO | 99/09946 | * 3/1999 |

OTHER PUBLICATIONS

Search Report under Section 17, Application No. GB 9902629.6, Apr./1999.

International Search Report Application No. PCT/EP 00/00759 mailed Jun. 28, 2000.

XP 002,139,746 & JP 07 061,913 (8/95)—Lion Corp (Derwent Abstract).

XP 002,139,745 & JP 54 134,711 (10/79)—Lion Fat & Oil Co., Ltd., Japan (Derwent Abstract).

XP 002,139,747 & JP 04 332,795 (11/92)—Lion Corp (Derwent Abstract).

* cited by examiner

Primary Examiner—Michael G. Hartley
Assistant Examiner—Sharmila S. Gollamudi
(74) Attorney, Agent, or Firm—Milton L. Honig

(57) ABSTRACT

Hair conditioning shampoo compositions are provided which contain a combination of conditioning agents including emulsified silicones, cationic polymers and certain fatty acid polyesters of polyols. Suitable fatty acid polyesters are sucrose pentalaurate, sucrose tetraoleate, sucrose pentaerucate, sucrose tetraerucate, sucrose tetrastearate, sucrose pentaoleate, sucrose octaoleate, sucrose pentatallowate, sucrose trirapeate, sucrose tetrarapeate, sucrose pentarapeate, sucrose tristearate and sucrose pentastearate, and mixtures thereof. The compositions give improved hair conditioning benefits, especially to hair which has been damaged, e.g. through environmental exposure or harsh mechanical or chemical treatments such as heat styling, perming or bleaching.

1 Claim, No Drawings

SHAMPOO COMPOSITIONS

This is a divisional of Ser. No. 09/496,574 filed Feb. 2, 2000, U.S. Pat. No. 6,350,441.

FIELD OF THE INVENTION

This invention relates to hair conditioning shampoo compositions containing a combination of conditioning agents including emulsified silicones, cationic polymers and certain fatty acid polyesters of polyols.

BACKGROUND AND PRIOR ART

The use of conditioning agents in hair shampoo formulations is well known and widely documented. A variety of conditioning agents have been described in this context, the principal classes of such agents being silicones, cationic polymers and oily materials such as hydrocarbons, higher alcohols, fatty acid esters, glycerides and fatty acids.

Fatty acid polyesters of cyclic polyols and/or sugar derivatives have been described as a component of hair conditioning formulations in the following documents:

WO98/04241 discloses that a conditioning system comprising a mixture of polyol carboxylic acid ester and particular nonionic water-soluble polymers is valuable in shampoo compositions for the delivery of improved hair feel and manageability. Cationic cellulose derivative polymer materials may be included in the compositions as optional ingredients.

WO96/37594 discloses a mild, foam producing personal cleansing composition with good skin feel attributes which is based on a combination of an oil dispersing nonionic surfactant and dispersed oil phase which is a mixture of a liquid polyol fatty acid polyester and the second oil component comprising one or more non-polar oils preferably selected from mineral oil, petrolatum, water-insoluble silicones, soya bean oils and mixtures thereof. The use of this mixed oil system is said to deliver improved skin feel.

WO98/04240 describes a shampoo composition containing a particular surfactant base of short chain alkyl sulphate and alkyl ethoxy sulphate in combination with a conditioning system comprising an insoluble oil conditioning agent selected from silicone materials, liquid polyol carboxylic acid esters and mixtures thereof.

JP-A-10/077,215 describes a cosmetic material consisting of saccharide fatty acid ester and one or more siloxanes selected from methyl polysiloxane, methyl phenyl siloxane and methyl polycyclosiloxane. The composition is said to provide good combing and feel after washing when used as a hair rinse or treatment.

A problem encountered with conditioning shampoo formulations is that the conditioning performance may be insufficient for many people, particularly in regions such as Japan and South East Asia where consumers desire a high level of conditioning and a "weighty" feel to their hair. Simply raising the level of conditioning agent in the formulation is not a satisfactory solution, since some conditioning agents tend to build up on the hair and be difficult to rinse off at high levels, leading to an undesirably slimy or coated feel.

To enhance conditioning efficacy, various combinations of conditioning ingredients in shampoo formulations have been proposed as follows:

Cationic polymers have been described for the enhancement of the deposition of silicone from a cleansing shampoo base in EP 0 432 951 and EP 0 529 883.

WO 93/08787 describes a tri-component conditioning system for delivery from shampoo composed of insoluble silicone, cationic polymer of specified charge density and an oily liquid for providing shine and lustre to the hair which is preferably selected from, inter alia, hydrocarbon oils such as paraffin oil and mineral oil, and alkyl/alkenyl esters of fatty acids such as isopropyl isostearate and isocetyl stearoyl stearate.

The present inventors have found that a specific combination of conditioning agents: emulsified silicones, cationic polymers and fatty acid polyesters of cyclic polyols and/or sugar derivatives, gives surprisingly improved overall conditioning compared to the various binary combinations of those individual ingredients which are disclosed in the prior art.

Furthermore, hair softness is particularly improved.

The compositions of the invention also have particular utility in the treatment of hair which has been damaged, e.g. through environmental exposure or harsh mechanical or chemical treatments such as heat styling, perming or bleaching. In such cases, the benefits of softness and ease of combing provided by compositions of the present invention are especially apparent.

SUMMARY OF THE INVENTION

The present invention provides an aqueous shampoo composition comprising, in addition to water:
 i) at least one cleansing surfactant chosen from anionic, zwitterionic and amphoteric surfactants or mixtures thereof, and
 ii) a combination of conditioning agents including:
   (a) emulsified particles of an insoluble silicone;
   (b) a cationic polymer, and
   (c) a fatty acid polyester of a polyol selected from cyclic polyols, sugar derivatives and mixtures thereof.

DETAILED DESCRIPTION AND PREFERRED EMBODIMENTS

Cleansing Surfactant

Shampoo compositions according to the invention will comprise one or more cleansing surfactants which are cosmetically acceptable and suitable for topical application to the hair. Further surfactants may be present as an additional ingredient if sufficient for cleansing purposes is not provided as emulsifying agent for the oily or hydrophobic components (such as silicones) present in the shampoo.

It is preferred that shampoo compositions of the invention comprise at least one further surfactant (in addition to that used as emulsifying agent) to provide a cleansing benefit.

Suitable cleansing surfactants, which may be used singularly or in combination, are selected from anionic, amphoteric and zwitterionic surfactants, cationic surfactants, and mixtures thereof. The cleansing surfactant may be the same surfactant as the emulsifier, or may be different. Preferred cleansing surfactants are selected from anionic, amphoteric and zwitterionic surfactants, and mixtures thereof.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight based on total weight.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO-(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyd chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifying agent) in shampoo compositions of the invention is generally from 0.1 to 50% by weight, preferably from 5 to 30%, more preferably from 10% to 25% by weight of the total shampoo composition.

Emulsified Particles of Insoluble Silicone

The silicone is insoluble in the aqueous matrix of the shampoo composition of the invention and so is present in an emulsified form, with the silicone present as dispersed particles.

Suitable silicones include polydiorganosiloxanes, in particular polydimethylsiloxanes which have the CTFA designation dimethicone.

Also suitable for use in compositions of the invention are hydroxyl functional silicones, in particular polydimethyl siloxanes having hydroxyl end groups which have the CTFA designation dimethiconol.

Also suitable for use in compositions of the invention are silicone gums having a slight degree of cross-linking, as are described for example in WO 96/31188. These materials can impart body, volume and stylability to hair, as well as good wet and dry conditioning.

A further preferred class of silicones for inclusion in shampoos of the invention are amino functional silicones. By "amino functional silicone" is meant a silicone containing at least one primary, secondary or tertiary amine group, or a quaternary ammonium group.

Examples of suitable amino functional silicones include:
(i) polysiloxanes having the CTFA designation "amodimethicone", and the general formula:

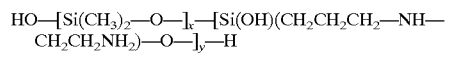

in which x and y are numbers depending on the molecular weight of the polymer, generally such that the molecular weight is between about 5,000 and 500,000.

(ii) polysiloxanes having the general formula:

in which:
G is selected from H, phenyl, OH or $C_{1-8}$ alkyl, e.g. methyl;
a is 0 or an integer from 1 to 3, preferably 0;
b is 0 or 1, preferably 1;
m and n are numbers such that (m+n) can range from 1 to 2000, preferably from 50 to 150;
m is a number from 1 to 2000, preferably from 1 to 10;
n is a number from 0 to 1999, preferably from 49 to 149, and
R' is a monovalent radical of formula —$C_qH_{2q}L$ in which q is a number from 2 to 8 and L is an aminofunctional group selected from the following:
—NR"—$CH_2$—$CH_2$—N(R")$_2$
—N(R")$_2$
—N$^+$(R")$_3$A$^-$
—N$^+$H(R")$_2$A$^-$
—N—H$_2$(R")A$^-$
—N(R")—$CH_2$—$CH_2$—N$^+$H$_2$(R")A$^-$
in which R" is selected from H, phenyl, benzyl, or a saturated monovalent hydrocarbon radical, e.g. $C_{1-20}$ alkyl, and;

A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

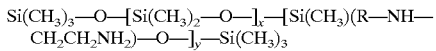
Si(CH$_3$)$_3$—O—[Si(CH$_3$)$_2$—O—]$_x$—[Si(CH$_3$)(R—NH—CH$_2$CH$_2$NH$_2$)—O—]$_y$—Si(CH$_3$)$_3$ wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

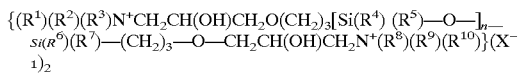
{(R$^1$)(R$^2$)(R$^3$)N$^+$CH$_2$CH(OH)CH$_2$O(CH$_2$)$_3$[Si(R$^4$) (R$^5$)—O—]$_n$—Si(R$^6$)(R$^7$)—(CH$_2$)$_3$—O—CH$_2$CH(OH)CH$_2$N$^+$(R$^8$)(R$^9$)(R$^{10}$)}(X$^-$1)$_2$ wherein R$^1$ and R$^{10}$ may be the same or different and may be independently selected from H, saturated or unsaturated long or short chain alk(en)yl, branched chain alk(en)yl and C$_5$–C$_8$ cyclic ring systems;

R$^2$ thru' R$^9$ may be the same or different and may be independently selected from H, straight or branched chain lower alk(en)yl, and C$_5$–C$_8$ cyclic ring systems;

n is a number within the range of about 60 to about 120, preferably about 80, and X$^-$ is preferably acetate, but may instead be for example halide, organic carboxylate, organic sulphonate or the like.

Suitable quaternary silicone polymers of this class are described in EP-A-0 530 974.

Amino functional silicones suitable for use in shampoos of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

An example of a quaternary silicone polymer useful in the present invention is the material K3474, ex Goldschmidt.

In general, the conditioning performance of the emulsified silicone in the shampoo composition of the invention tends to increase with increased viscosity of the silicone itself (not the emulsion or the final shampoo composition).

For dimethicone and dimethiconol-type silicones, the viscosity of the silicone itself is typically at least 10,000 cst, preferably at least 60,000 cst, most preferably at least 500,000 cst, ideally at least 1,000,000 cst. Preferably the viscosity does not exceed 10$^9$ cst for ease of formulation. For amino functional-type silicones, the viscosity of the silicone itself is not particularly critical and can suitably range from about 100 to about 500,000 cst.

Emulsified silicones for use in hair shampoos of the invention will typically have an average silicone particle size in the composition of less than 30, preferably less than 20, more preferably less than 10 microns. In general, reducing the silicone particle size tends to improve conditioning performance. Most preferably the average silicone particle size of the emulsified silicone in the composition is less than 2 microns, ideally it ranges from 0.01 to 1 micron. Silicone emulsions having an average silicone particle size of <0.15 microns are generally termed microemulsions.

Particle size may be measured by means of a laser light scattering technique, using a 2600D Particle Sizer from Malvern Instruments.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

Pre-formed emulsions of amino functional silicone are also available from suppliers of silicone oils such as Dow Corning and General Electric. Particularly suitable are emulsions of amino functional silicone oils with non ionic and/or cationic surfactant. Specific examples include DC929 Cationic Emulsion, DC939 Cationic Emulsion, DC949 Cationic emulsion, and the non-ionic emulsions DC2-7224, DC2-8467, DC2-8177 and DC2-8154 (all ex Dow Corning).

Mixtures of any of the above types of silicone may also be used. Particularly preferred are hydroxyl functional silicones, amino functional silicones and mixtures thereof.

The total amount of silicone incorporated into compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy.

When the silicone is incorporated as a pre-formed emulsion as described above, the exact quantity of emulsion will of course depend on the concentration of the emulsion, and should be selected to give the desired quantity of silicone in the final composition.

Cationic Polymer

A cationic polymer is an essential ingredient in shampoo compositions of the invention, for enhancing conditioning performance of the shampoo.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymer will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides(as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use In compositions of the invention include those of the formula:

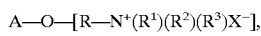

A—O—[R—N⁺(R¹)(R²)(R³)X⁻], wherein: A is an anhydroglucose residual group, such as a starch or cellulose anhydroglucose residual. R is an alkylene, oxyalkylene, polyoxyalkylene, or hydroxyalkylene group, or combination thereof. R¹, R² and R³ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R¹, R² and R³) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17, having a high degree of substitution and a high viscosity, JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar gum derivatives.

Fatty Acid Polyester

A further essential component in shampoo compositions of the invention is a fatty acid polyester of a polyol selected from cyclic polyols, sugar derivatives and mixtures thereof.

By "polyol" is meant a material having at least four hydroxyl groups. The polyols used to prepare the fatty acid polyester will preferably have from 4 to 12, more preferably from 4 to 11, most preferably from 4 to 8 hydroxyl groups.

By "fatty acid polyester" is meant a material in which at least two of the ester groups are independently of one another attached to a fatty (C₈ to C₂₂ alkyl or alkenyl) chain. For a given material, prefixes such as "tetra-", "penta-" indicate the average degrees of esterification. The compounds exist as a mixture of materials ranging from the monoester to the fully esterified ester.

Cyclic polyols are the preferred polyols used to prepare the fatty acid polyester in the present invention. Examples include inositol, and all forms of saccharides. Saccharides, in particular monosaccharides and disaccharides, are especially preferred.

Examples of monosaccharides include xylose, arabinose, galactose, fructose, sorbose and glucose. Glucose is especially preferred.

Examples of disaccharides include maltose, lactose, cellobiose and sucrose. Sucrose is especially preferred.

Examples of suitable sugar derivatives include sugar alcohols, such as xylitol, erythritol, maltitol and sorbitol, and sugar ethers such as sorbitan.

The fatty acids used to prepare the fatty acid polyester in the present invention have from 8 to 22 carbon atoms. They can be branched or linear, and saturated or unsaturated.

Examples of suitable fatty acids include caprylic, capric, lauric, myristic, myristoleic, palmitic, palmitoleic, stearic, 12-hydroxystearic, oleic, ricinoleic, linoleic, linolenic, arachidic, arachidonic, behenic, and erucic acids. Erucic acid is particularly preferred.

Mixed fatty acid moieties from source oils which contain substantial amounts of the desired unsaturated or saturated acids can be used as the acid moieties to prepare fatty acid polyesters suitable for use in the hair treatment composition of the invention. The mixed fatty acids from the oils should contain at least 30%, preferably at least 50% of the desired unsaturated acids. For example, high erucic rapeseed oil fatty acids can be used instead of pure C20–C22 unsaturated acids, and hardened, i.e. hydrogenated, high erucic rapeseed oil fatty acids can be used instead of pure C20–C22 saturated acids. Preferably the C20 and higher acids, or their derivatives, e.g. methyl or other lower alkyl esters, are concentrated, for example by distillation. The fatty acids from palm kernel oil or coconut oil can be used as a source of C8 to C12 acids, and those from cotton seed oil and soya bean oil as a source of C16 to C18 acids.

Specific examples of suitable fatty acid polyesters are sucrose pentalaurate, sucrose tetraoleate, sucrose pentaerucate, sucrose tetraerucate, sucrose tetrastearate, sucrose pentaoleate, sucrose octaoleate, sucrose pentatallowate, sucrose trirapeate, sucrose tetrarapeate, sucrose pentarapeate, sucrose tristearate and sucrose pentastearate, and mixtures thereof. Sucrose pentaerucate and sucrose tetraerucate are particularly preferred. These materials are available commercially as Ryoto Sugar Esters ex Mitsubishi Kasei Foods.

It is also advantageous if the ester groups of the fatty acid polyester are independently of one another attached to a fatty ($C_8$ to $C_{22}$ alkyl or alkenyl) chain or a short chain alkyl ($C_2$ to $C_8$) chain and in which the number ratio of $C_8$ to $C_{22}$ groups to $C_2$ to $C_8$ groups in the fatty acid polyester molecule ranges from 5:3 to 3:5, preferably from 2:1 to 1:2, more preferably about 1:1. The polyol used to prepare such a material is preferably a saccharide, most preferably glucose, with at least five of the hydroxyl groups being esterified. These products are in the main oils and are thus easy to formulate. Specific examples are glucose penta esters where about 50% by number of the ester groups are acetyl groups and about 50% by number of the ester groups are octanoyl, decanoyl or dodecanoyl groups respectively. The synthesis of this type of material is described in WO98/16538.

The fatty acid polyester can be prepared by a variety of methods well known to those skilled in the art. These methods include acylation of the cyclic polyol or reduced saccharide with an acid chloride; trans-esterification of the cyclic polyol or reduced saccharide fatty acid esters using a variety of catalysts; acylation of the cyclic polyol or reduced saccharide with an acid anhydride and acylation of the cyclic polyol or reduced saccharide with a fatty acid. Typical preparations of these materials are disclosed in U.S. Pat. No. 4,386,213 and AU 14416/88.

The total amount of fatty acid polyester in hair treatment compositions of the invention is generally from 0.001 to 10% by weight, preferably from 0.01 to 5%, more preferably from 0.01% to 3% by weight of the total hair treatment composition.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glucamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

free fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g. lanolin.

Mixtures of any of the above active ingredients may also be used.

The invention is further illustrated by way of the following non-limitative Examples, in which all percentages quoted are by weight based on total weight unless otherwise stated.

EXAMPLES

Example 1

Salon Evaluation

The following shampoo formulations were prepared:

| Ingredient | Example 1 (wt%) | Comparative Ex. A (wt%) |
|---|---|---|
| Sodium lauryl ether sulphate 2EO (SLES) | 14.0 | 14.0 |
| Cocamidopropyl betaine (CAPB) | 2.0 | 2.0 |
| JAGUAR ® C13S | 0.2 | 0.2 |
| CARBOPOL ® ETD 2020 | 0.4 | 0.4 |
| Silicone emulsion[1] | 1.5 | 1.5 |

-continued

| Ingredient | Example 1 (wt%) | Comparative Ex. A (wt%) |
|---|---|---|
| EUPERLAN ® PK3000[2] | 6.0 | 6.0 |
| Sucrose tetraerucate[3] | 0.025 | — |
| Preservative, colour, fragrance | q.s | q.s. |
| Water, minors | to 100% | to 100% |

[1]Added as DC2-1766 (emulsion of dimethiconol in anionic surfactant, 60% active, ex Dow Corning)
[2]Glycol stearate pearlizer, (ex Henkel)
[3]Added as Ryoto Sugar ER290 (ex Mitsubishi Kasei Foods)

Methodology: Salon test using ½ head test and 36 panellists

Results: Significant wins on hair softness were judged by the hairdresser and panellist (10% and 5% win respectively) for Example 1 compared with Comparative Example A.

Example 2

Switch Testing

A pair of shampoo formulations were made up having the following formulations:

| | Example 2 (wt %) | Comparative Example B (wt %) |
|---|---|---|
| SLES | 14 | 14 |
| CAPB | 2 | 2 |
| JAGUAR ® C13S | 0.3 | 0.1 |
| CARBOPOL ® ETD 2020 | 0.4 | 0.4 |
| Sucrose tetraerucate[3] | 1 | 0 |
| Glycerol | 2 | 2 |
| Silicone emulsion[1] | 1 | 2 |
| Water, minors | q.s. | q.s. |

The formulations of Example 2 and Comparative Example B were submitted to a paired test over a range of conditioning attributes. Panellists voted for their preferred formulation from the pair for each conditioning attribute and the results are shown in the following Table:

| Paired test | % of votes | |
|---|---|---|
| Smooth wet | 54% | 45% |
| Ease of comb wet | 57% | 46% |
| Smooth dry | 56% | 44% |
| Ease of comb dry | 51% | 49% |
| Flyaway | 51% | 49% |

It is apparent that the formulation of Example 2 was preferred by the panellists to the Comparative Example over all attributes tested.

Example 3

Switch Testing

A further pair of shampoo formulations were made up having the following formulations:

| | Example 3 (wt %) | Comparative Example C (wt %) |
|---|---|---|
| SLES | 14 | 14 |
| CAPB | 2 | 2 |
| JAGUAR ® C13S | 0.1 | 0.1 |
| CARBOPOL ® ETD 2020 | 0.4 | 0.4 |
| Sucrose tetraerucate[3] | 1 | 2 |
| Glycerol | 2 | 2 |
| Silicone emulsion[1] | 1 | 0 |
| Water, minors | q.s. | q.s. |

The formulations of Example 3 and Comparative Example C were submitted to a paired test as in the previous Example. The results are shown in the following Table:

| Paired test | % of votes | |
|---|---|---|
| Smooth wet | 78% | 22% |
| Ease of comb wet | 89% | 11% |
| Smooth dry | 68% | 32% |
| Ease of comb dry | 75% | 25% |
| Flyaway | 56% | 44% |

It is apparent that the formulation of Example 3 was preferred by the panellists to the Comparative Example over all attributes tested.

What is claimed is:

1. An aqueous shampoo composition comprising:
   i) at least one cleansing surfactant chosen from anionic, zwitterionic and amphoteric surfactants or mixtures thereof, and;
   ii) a combination of conditioning agents including:
      (a) emulsified particles of an insoluble silicone;
      (b) a cationic polymer;and
      (c) a fatty acid polyester of a polyol selected from the group consisting of sucrose pentaerucate, sucrose tetraerucate and mixtures thereof.

* * * * *